United States Patent [19]
Fishman et al.

[11] Patent Number: 5,179,959
[45] Date of Patent: Jan. 19, 1993

[54] ALLERGY TESTING APPARATUS AND METHOD

[75] Inventors: Henry Fishman, Washington, D.C.; Robert Olshaker, San Diego, Calif.; Gary Johnson, New York, N.Y.

[73] Assignee: Henry Fishman, Washington, D.C.

[21] Appl. No.: 780,128

[22] Filed: Oct. 29, 1991

Related U.S. Application Data

[63] Continuation of Ser. No. 626,236, Dec. 11, 1990, Pat. No. 5,076,282, which is a continuation of Ser. No. 532,239, May 29, 1990, abandoned, which is a continuation of Ser. No. 113,364, Oct. 21, 1987, abandoned, which is a continuation-in-part of Ser. No. 853,748, Apr. 18, 1986, abandoned.

[51] Int. Cl.$^5$ ................................. A61B 5/00
[52] U.S. Cl. .................... 128/743; 604/47; 606/186
[58] Field of Search ............ 128/743; 606/160, 161, 606/167, 172, 181, 185, 186; 604/46, 47

[56] References Cited

U.S. PATENT DOCUMENTS

| | | |
|---|---|---|
| 2,841,138 | 7/1958 | Laub . |
| 3,289,670 | 12/1966 | Krug et al. . |
| 3,515,126 | 6/1970 | Fregert .................. 128/743 |
| 3,894,531 | 7/1975 | Saunders, Jr. ............. 128/743 |
| 3,999,543 | 12/1976 | Lacey . |
| 4,168,701 | 9/1979 | Chiulli . |
| 4,270,548 | 6/1981 | Brennan . |
| 4,292,979 | 10/1981 | Inglefield et al. . |
| 4,390,027 | 6/1983 | Alani et al. ............... 128/743 |
| 4,453,926 | 6/1984 | Galy . |
| 4,802,493 | 2/1989 | Maganias ................. 128/743 |
| 4,818,707 | 4/1989 | Breneman ................ 128/743 |
| 4,966,159 | 10/1990 | Maganias ................. 128/743 |

FOREIGN PATENT DOCUMENTS

913485 10/1972 Canada .
325001 10/1902 France .

Primary Examiner—William E. Kamm
Assistant Examiner—John P. Lacyk
Attorney, Agent, or Firm—Frishaus, Holtz, Goodman & Woodward

[57] ABSTRACT

An allergy testing system, for testing a patient for a plurality of allergies at substantially the same time, comprises a housing containing a plurality of packages or capsules containing an allergen and a needle, the needles being spaced apart from each other. The needles preferably carry the respective allergens on their tips. The housing is placed against the skin of a patient and an actuator is operated to engage the packages to move the needles to pierce or prick the skin of the patient, thereby applying the respective allergens to the pierced or pricked skin of the patient.

6 Claims, 10 Drawing Sheets

ALLERGY TESTING APPARATUS AND METHOD

CROSS-REFERENCE TO RELATED APPLICATIONS

This is a continuation of application Ser. No. 07/626,236 filed Dec. 11, 1990, now U.S. Pat. No. 5,076,282 which is a continuation of application Ser. No. 532,239, filed May 29, 1990 (abandoned), which is a continuation of application Ser. No. 07/113,364, filed Oct. 21, 1987 (abandoned), which is a continuation-in-part of application Ser. No. 06/853,748, filed Apr. 18, 1986 (abandoned).

BACKGROUND OF THE INVENTION

This invention relates to allergy testing methods and apparatuses for testing a patient for a plurality of allergies at substantially the same time.

Allergy testing generally involves giving a patient a plurality of "prick tests." Each prick test is applied in order to determine whether or not a patient is allergic to a particular substance, such as pollen, animal dander, dust, foods, etc. A conventional prick test involves placing a drop of a test substance on the patient's skin and then using a needle to scratch the substance through the skin. If a reaction occurs, the patient is considered to be allergic to the particular substance. At present, allergy testing is carried out on an individual basis. Each test stubstance is dropped, one drop at a time, on the patient's arm or back. Each drop is then individually pricked through the skin with a separate needle. This is a very time consuming process (for both the patient and the practitioner) and very often involves multiple office visits for the patient This leads also to a substantial amount of patient discomfort, expense, and inconvenience.

The object of the present invention is to provide improved apparatuses and methods for testing patients for allergic reactions to a plurality of substances, all at substantially the same time.

A further object of the invention is to provide improved apparatuses which are easily produced and easily used without requiring a great deal of technical skill on the part of the operator.

Yet another object of the invention is to provide improved apparatuses which used pre-packaged allergens and needles, which are easily insertible in and removable from a carrier, thereby facilitating loading the carrier with predetermined allergens, and improving the sterility of the apparatus.

Still another object is to provide an allergy testing system where the pricking of the skin is always done to a given skin penetration depth which is predictable and which is replicable without requiring highly skilled operators.

SUMMARY OF THE INVENTION

According to the present invention, an allergy testing apparatus for testing a patient for a plurality of allergies at substantially the same time, comprises: a plurality of allergen applying means, each including a source of allergen, a support member, a top member movably coupled to the support member, and piercing means coupled to the top member and being movable, responsive to movement of the top member, from an inactive to an active position for piercing the skin of a patient and applying an allergen to the skin of the patient when moved from the inactive position to the active position; a housing having at least one receptacle for receiving and supporting the plurality of allergen applying means with a given spacing between each of the piercing means; and actuating means coupled to the housing for moving the top member of each allergen applying means to move the piercing means of the associated allergen applying means from the inactive position to the active position thereof to pierce the skin of a patient and to thereby apply an allergen from a respective allergen applying means to the skin of the patient.

According to a further aspect of the invention, a method for testing a patient for a plurality of allergies at substantially the same time, comprises:

providing a plurality of allergen applying means, each including a source of allergen, a support member, a top member movably coupled to the support member, and piercing means coupled to the top member, from an inactive to an active position for piercing the skin of a patient and applying an allergen to the skin of the patient when moved from the inactive position to the active position; placing the allergen applying means in at least one receptacle of a housing for supporting the plurality of allergen applying means with a given spacing between each of the piercing means; and then moving the top member of each allergen applying means to move the piercing means of the associated allergen applying means from the inactive position to the active position thereof to pierce the skin of a patient and to thereby apply an allergen from a respective allergen applying means to the skin of the patient.

DETAILED DESCRIPTION

Figure 1:
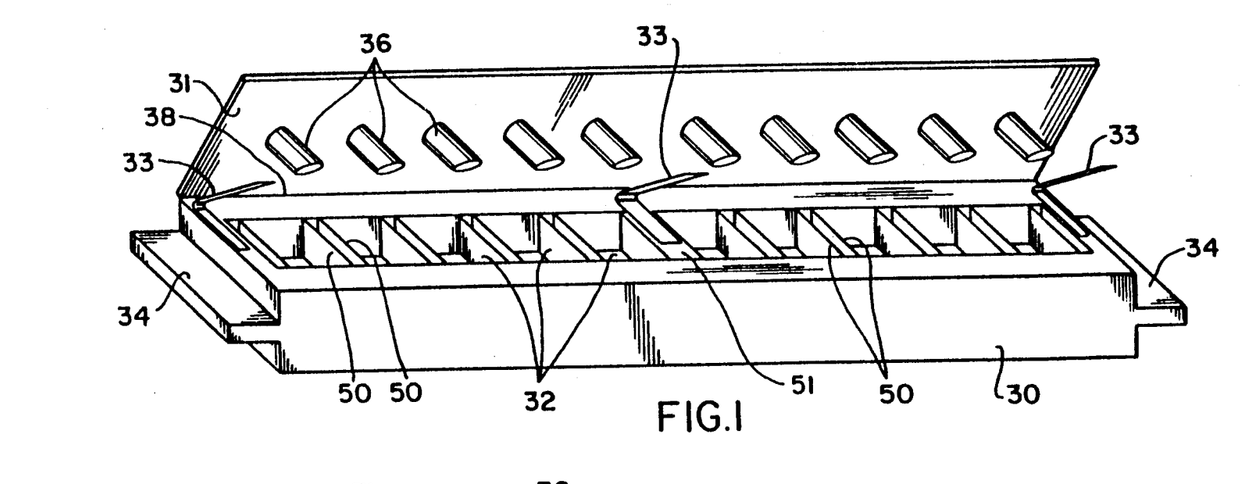
FIG. 1 is a perspective view of a first embodiment of the present invention.
Figure 2:
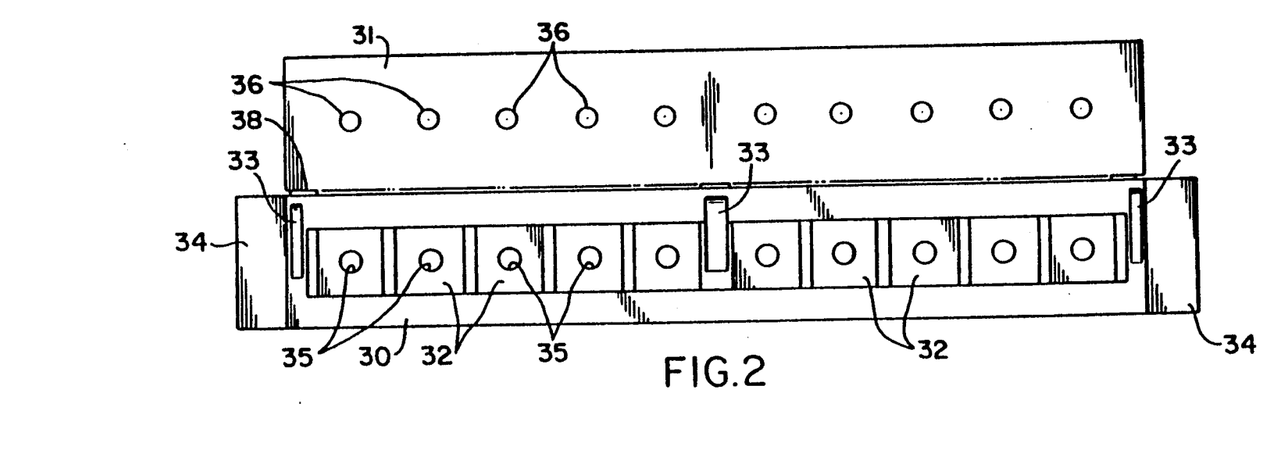
FIG. 2 is a top view thereof with the top cover member in its fully opened position ready to receive allergen containers.
Figures 3, 4, 5, 6, 7:
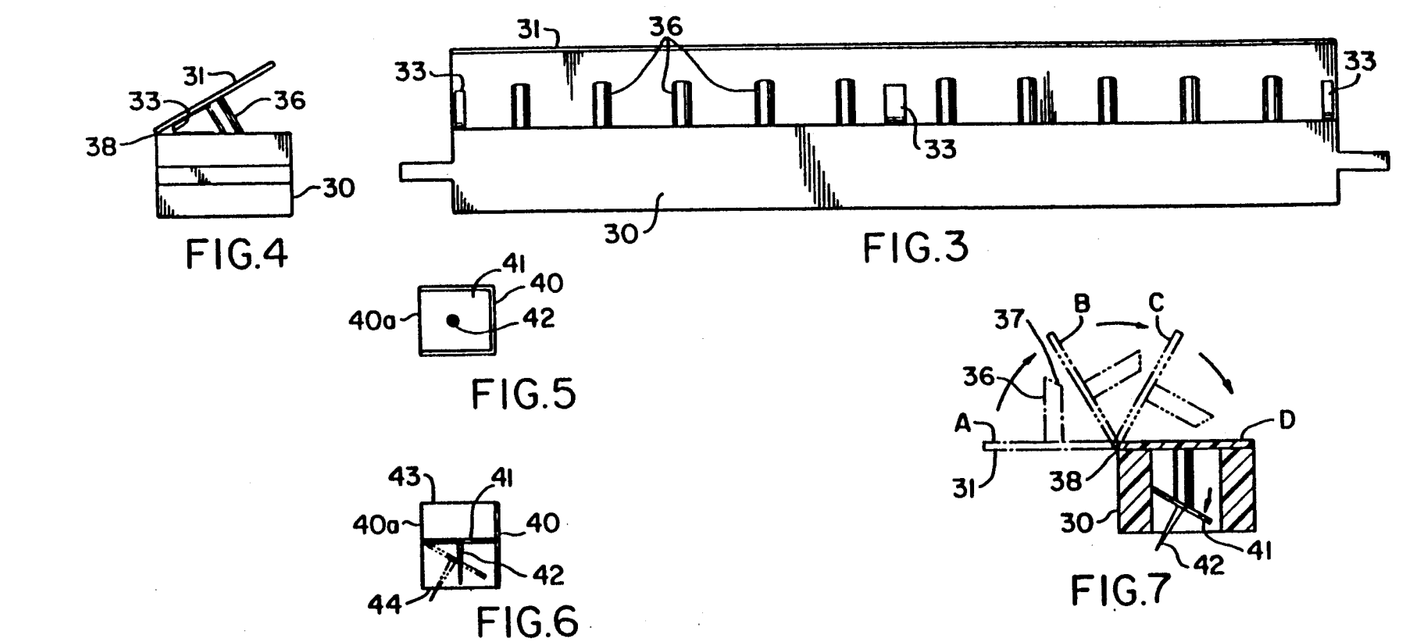
FIG. 3 is a front elevational view thereof with the top cover member partially closed in its "ready for activation" position.
FIG. 4 is a side elevational view in the same condition as shown in FIG. 3.
FIG. 5 is a top view of an allergen container for use with the device of FIGS. 1-4.
FIG. 6 is a sectional view of the allergen container of FIG. 5.
FIG. 7 is a sectional view of the embodiment of FIGS. 1-6, showing the top cover member in its fully opened position and in its fully closed position in solid lines, and in intermediate positions in dashed lines.

Referring to FIGS. 1-4, an allergy testing apparatus comprises an elongated housing 30 having a cover member 31 hingedly connected thereto, preferably by means of a "living hinge" 38. Preferably, the living hinge 38 extends along the complete length of the elongated housing and cover member, but it may be provided in small sections as shown in FIG. 2. The housing 30 defines a plurality of compartments 32 for receiving respective packages or capsules containing allergens and/or an allergen applying needle. Holes or openings 35 are provided at the bottom of each respective compartment 32. Springs 33 (preferably leaf springs) are provided on the upper surface of the housing 30 for resiliently biasing the cover member in a partially open position as shown in FIG. 4. The cover member 31 may be moved further downwardly relative to the housing 30 upon application of a closing force to the cover member 31 which operates against the biasing force of the springs 33. This will be described hereinbelow with respect to FIG. 7.

Figure 25:
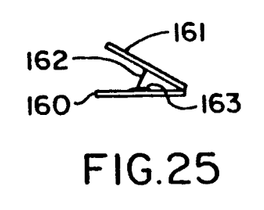
FIG. 25 is a side view of a modified allergen carrying member for use with the embodiment of FIGS. 9-14.
Figure 26:
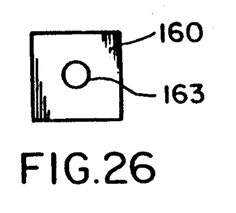
FIG. 26 is a top view of the bottom member of the allergen carrying member of FIG. 25, the top member being removed for ease of illustration.
Figure 27:
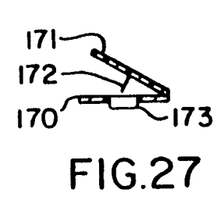
FIG. 27 shows a sectional view of a further modified allergen carrying member for use with the embodiment of FIGS. 9-14.

The housing is provided with projecting handle portions 34 at opposite ends thereof for use in handling the device, before, after and during allergy testing. The cover member 31 comprises a plurality of projections 36 extending downwardly therefrom. Projections 36 are used in actuating the allergen applying package or capsule which is placed in the respective compartments 32 of the housing 30. This will be described further hereinbelow. FIGS. 5 and 6 illustrate an allergen containing capsule which comprises a rectangular tubular member 40, preferably made of plastic, such as styrene which may be, for example, 1/32 inches thick. Hingedly or pivotally connected to one internal wall of the tubular member 40 in a horizontal plastic member 41 having a needle 42 projecting downwardly therefrom. The needle is preferably sealed within the plastic rectangular tube by means of a plastic covering 43,44, at the upper and lower ends thereof, respectively. The tip of the needle is preferably coated with an allergen at the factory before the upper and lower seals 43,44 are applied. However, allergens could be provided in the manner shown in FIGS. 25-27. The upper and lower seals 43,44 are preferably very thin and are easily puncturable. The apparatus is used by placing capsules 40, each containing a different allergen, in the respective compartments 32 of housing 30. After the capsules 40 are placed in the respective compartments 32 (see FIG. 7), the cover member 31 can be closed over the capsules so that the projections 36 of the cover member break the upper seal 43 and bear down on the horizontal member 41 to push it downwardly to the dashed line position shown in FIG. 7. When the horizontal member 41 and the needle 42, of the respective capsules move downwardly to the dashed line position, the needle punctures the lower seal 44 and pierces or pricks the skin of the patient to apply the allergen to the pierced or pricked skin portion of the patient. In FIG. 7, the cover 31 is shown in position A at its open position (most counterclockwise position), at which time the compartments 32 of the housing 30 can be loaded with respective capsules 40 containing respective different allergens. After loading the respective capsules in the compartments 32 the housing 30 is placed against the skin of the patient and is held in place by the operator via handles 34. Then, the cover member 31 is moved through positions B and C (shown in dashed lines) to the closed position C (shown in solid lines). When the cover is moved to the closed position D, against the biasing force of the springs 33, the projections 36 first puncture the upper seal 43 of their respective capsule, then push the respective horizontal member 41 and needle 42 downwardly so that the needle 42 punctures the lower seal 44, and passes through the respective hole or opening 35, since at this time the housing 30 is held against the skin of a patient, the needle 42 will pierce or prick the skin of the patient after puncturing the lower seal 44 and passing through the respective hole 35 in the lower portion of the housing 32. In this manner, the allergen at the tip of the needle or on the base as shown in FIGS. 25-27 (factory applied) is applied to the pricked or pierced skin portion of the patient. Upon releasing the cover member 31 (when it is in the closed position D), the springs 33 will lift the cover 31 upwardly to the position shown in FIG. 4, thereby withdrawing the needles from the skin of the patient and into the interior of the compartments 32 of the housing 30.

After use, the housing 30 can be sterilized and reloaded with fresh allergen containing capsules, ready for the next use.

The projections 36 may be in the form of rods, and may have inclined lower surfaces 37 as shown in FIG. 7. The inclined lower surfaces 37 provide a better surface contact with the pivotal member 41 of the capsule, as shown in FIG. 7.

The housing 30 and cover 31 are preferably fabricated of plastic as a single unit by means of injection molding. Suitable plastic materials are, for example, polyvinylchloride (PVC), nylon, polycarbonate or the like.

Figure 8:
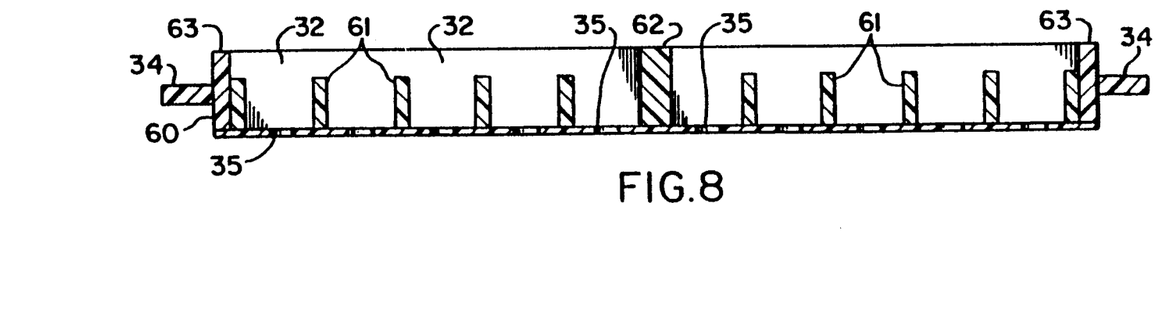
FIG. 8 is a sectional view of the housing portion of the apparatus of FIG. 1, but showing a modification to the internal construction thereof.

FIG. 8 shows a sectional view taken through the longitudinal center of the housing 30, but showing a modified embodiment. In the housing of FIG. 1, the compartments 32 are separated by respective pairs of walls 50. The central wall 51 is solid for supporting a spring 33 thereon. It should be clear that the embodiment of FIGS. 1-7 could be modified by providing only a single wall 50 between adjacent compartments 32. In the description of FIG. 8, like reference numerals will be used for parts which are similar to those parts described earlier.

The embodiment of FIG. 8 comprises a housing 60 which is substantially similar to the housing 30 of FIGS. 1-4. The housing comprises a plurality of walls 61 defining a plurality of compartments 32 therebetween. Holes 35 are provided in the bottom of housing 60 for passage of a needle there through, in the same manner as shown in FIG. 7. The central wall 62 of the housing 60 is substantially the same height as the end walls 63 of the housing. Springs 33 are placed on top of the end walls 63 and central wall 62, in a manner similar to that shown in FIG. 1.

The embodiment of FIG. 8 preferably has a cover member 31 integrally formed therewith and connected thereto via a living hinge, as in the embodiment of FIGS. 1-4.

In the foregoing embodiments, the cover member 31 could be provided separately, and connected to the housing by means of hinges or other pivotal connecting means.

Figure 9:
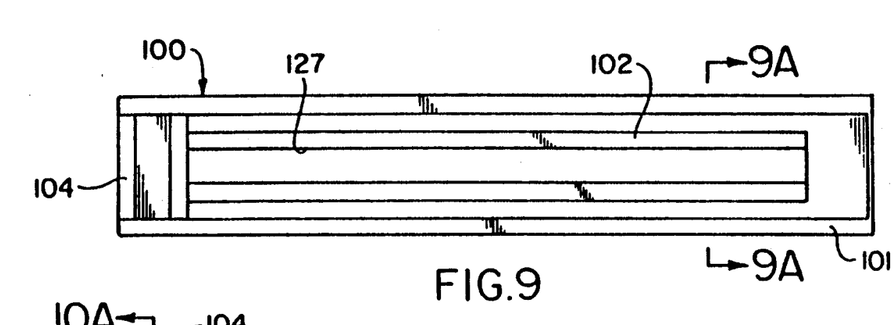
FIG. 9 is a top view of a second embodiment of the invention.
Figure 9A:
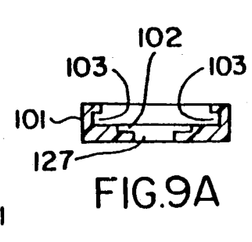
FIG. 9A is a sectional view taken along the line 9A—9A in FIG. 9.
Figure 10:
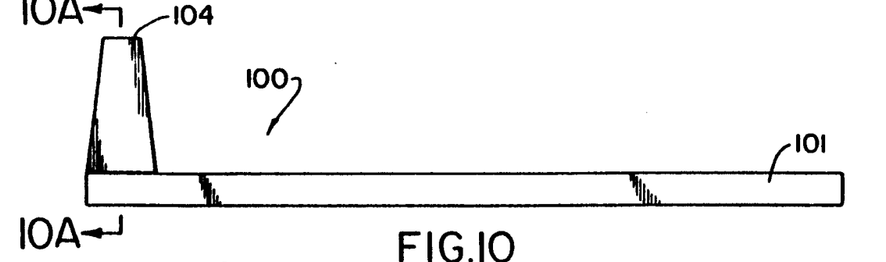
FIG. 10 is a side view of the embodiment of FIG. 9.

FIGS. 9 and 10 are top and side views, respectively, of a modified unit 100 for carrying out a plurality of allergy tests. FIGS. 9 and 10 illustrate the holding unit and operating members, and FIGS. 11, 12 and 13 illustrate removable cassettes which are removably received in the holding unit of FIGS. 9 and 10.

Referring to FIGS. 9, 9A, 10 and 10A, the holding unit comprises a rectangular base member 101 having a trough 102 (see FIG. 9A) therein for receiving cassettes (of FIGS. 11-13) containing allergens. The base member 101 also comprises a pair of grooves 103 extending along the length thereof (see FIG. 9A) for receiving an operating member 104 therein. The operating member 104 has side rails 105 extending along the length thereof which are guided in the grooves 103 of the base member 101. See FIG. 10A. The operating member 104 is slidable along the length of the base portion 101, with its side rails 105 guided in the elongated grooves 103 of the base member 101.

Figure 11:
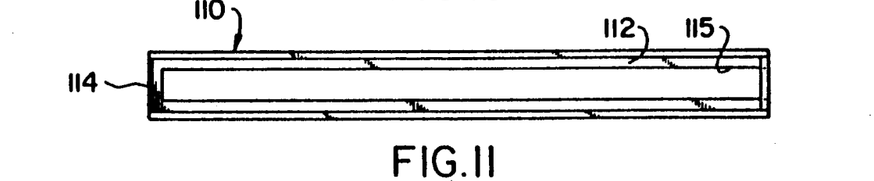
FIG. 11 is a top view of a cassette for use with the embodiment of FIGS. 11 and 12.
Figure 11A:
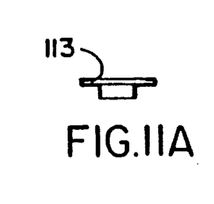
FIG. 11A is an end view of the cassette of FIG. 11.
Figure 12:
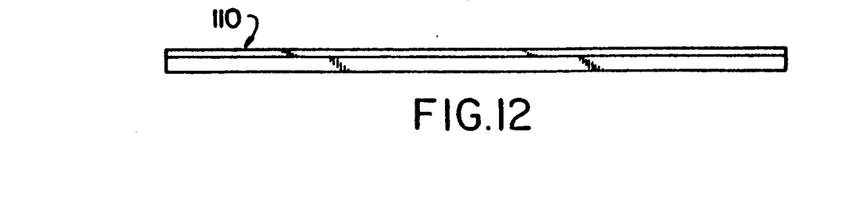
FIG. 12 is a side view of the cassette of FIG. 11.
Figures 13, 14, 15, 16, 17, 18, 22, 23:
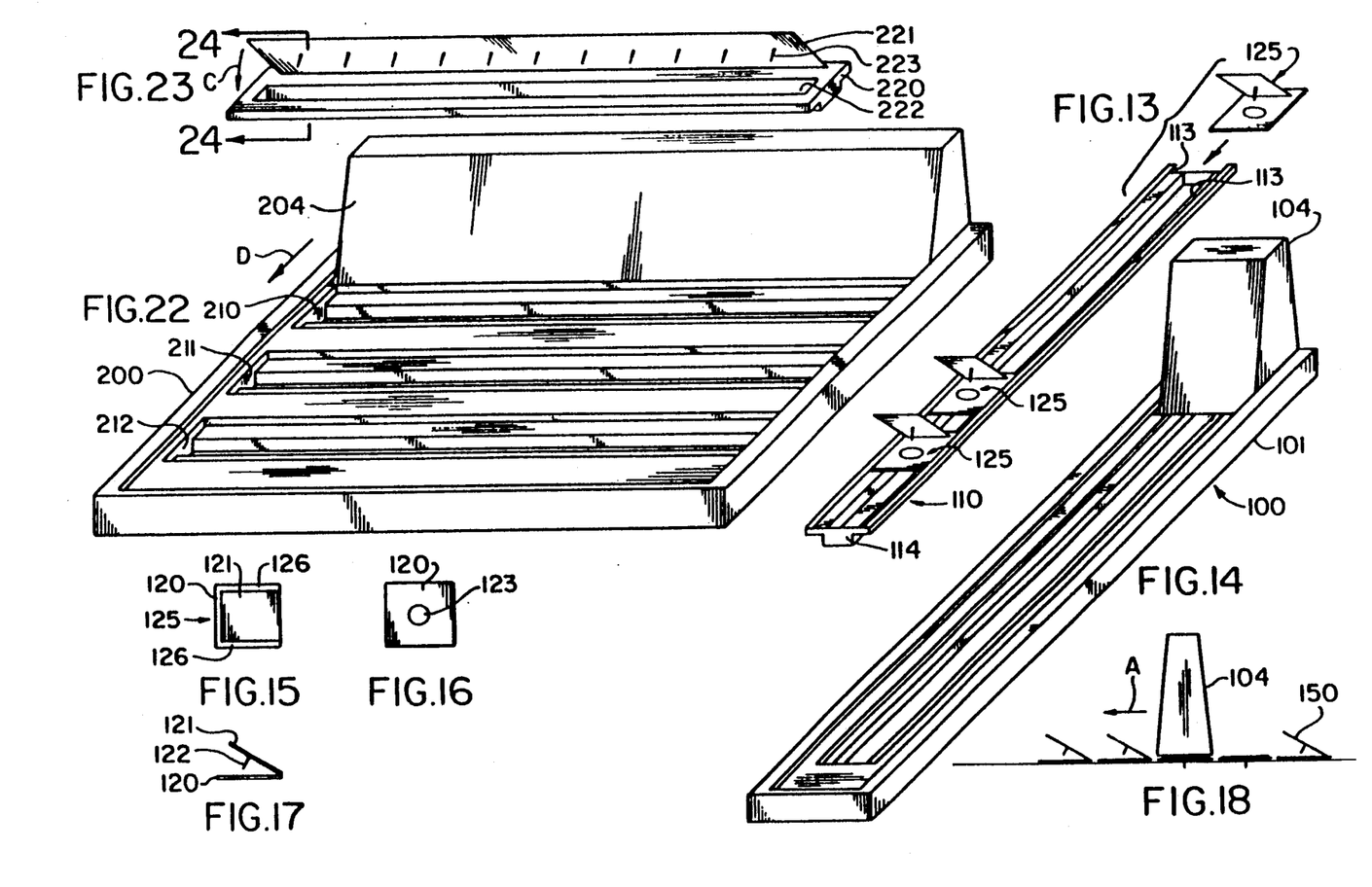
FIG. 13 is a perspective view of the cassette of FIGS. 11 and 12, partially loaded.
FIG. 14 is a perspective view of the unit of FIGS. 9 and 10.
FIGS. 15-17 are top, bottom and side views of an allergen carrying member for use with the embodiment of FIGS. 9-14.
FIG. 18 is a schematic view showing the embodiment of FIGS. 9-14 in use.
FIG. 22 is a perspective view of the embodiment of FIGS. 19 and 20.
FIG. 23 is a perspective view of a cassette for use with the embodiment of FIGS. 19-22.

The removable cassette, shown in FIGS. 11-13, is configured to fit within the trough 102 of the base member 101. The cassette 110 has an elongted trough 112 formed therein for receiving capsules or packages 125 of allergens, as shown in FIG. 13. The capsules or packages 125 of allergen are described below with references to FIGS. 15-17. The cassette 110 has side edges forming grooves 113 (see FIG. 11), into which the rectangular packages 125 of allergen are slidable. A stop 114 is provided at one end of the cassette to prevent the allergen packages from sliding off the end thereof. After the cassette is loaded with allergen packages 125 as shown in FIG. 13 (preferably, the allergen packages 125 are loaded along the complete length of cassette 110), the loaded cassette is placed within the trough 102 of the base member 101. When placing the cassette in the base member 101, the end with the stop 114 thereon is placed toward the right as seen in FIGS. 9 and 10, remote from the operating member 104. When in this condition, the tops 121 of the allergen packages 125 (see FIGS. 15-17) provide inclined planes along which the operating unit 104 slides so as to press the inclined tops 121 of the allergen packages 125 downward, thereby causing the needles 122 in the allergen packages to be extended through the opening 123 of the lower surface of the package 125 through the opening 115 of the cassette to thereby pierce or prick the skin of the patient, while simultaneously applying the allergen contained within the package 125 to the pierced or pricked skin of the patient. The allergen can be applied to the needle tip at the factory as will be described below.

Stop 114 can be movable to accommodate fewer than the maximum number of allergen packages which can be received in the device. Alternatively, dummy or blank packages containing no allergen or needle, or a flat appropriately sized plate can be inserted in trough 12 to serve as a space filling member when fewer than the maximum number of allergen packages are used.

FIGS. 15-17 show top, bottom and side views of the allergen carrying rectangular packages or capsules 125 for use in the embodiment of FIGS. 9-14. The rectangular packages 125 each comprise a substantially rigid plastic base member 120 with a substantially rigid preferably plastic top member 121 which is hingedly or pivotally connected to the base member 120, as shown in FIG. 17. Preferably, the connection between base 120 and top 121 is by means of a living hinge. The top member 121 has a needle 122 secured to the underside thereof as seen best in FIG. 17. The bottom member 120 has a hole 123 in the bottom surface thereof in registration with the needle 122. The bottom member 120 is larger than the top member 121 so as to provide a flange portion 126 on each side of the package 125 to slide in the grooves 113. The top member 121 has a width so that it can be pressed down between the side rails forming the grooves 113.

In operation, the base member is loaded with a cassette 110 and is placed against the skin of a patient. Then, as the operating unit 104 is passed over the rectangular package 125 in the cassette, the top members 121 are pressed downwardly (see FIG. 18) and the needle 122 of the respective packages 125 passes through the hole 123 and through the opening 115 in the trough of the cassette 110 (and therefore through opening 127) so as to pierce or prick the skin of the patient. Preferably, the rectangular packages or capsules 125 of FIGS. 15-17 are one-piece moulded plastic structures with a 30 gauge, ⅜ inch long needle 122 secured to the underside of the top member 121. An allergen is preferably placed on the needle tips in the factory during manufacture, and the entire wedge-shaped unit is sealed in cellophane or other suitable sealing materials which are puncturable by the needle 122. When the device is operated, the needles 122 pierce the wrapping of the package to apply the allergen to the skin of the patient. The top of the upper member 121 is marked at the factory with the type of allergen which is on the needle tip. The marking can be accomplished by imprinting or applying a label to the top of the rectangular member. The lower and upper surfaces 120,121 are preferably made of a flexible polyvinylchloride (PVC) material for a natural spring-effect so that the members remain sprung outwardly as shown in FIG. 16 when not in use. The angle between the lower member 120 and the top member 121 is preferably 30°. but this angle could be varied, depending upon application.

FIG. 18 schematically shows the apparatus in use. As the wedge-type operating member 104 is moved in the direction of the arrow A in FIG. 17, it forces the upper surfaces of the rectangular packages downwardly and thereby forces the needles 122 to extend through the bottom opening in the trough and pierce or prick the skin, thereby applying the allergen on the needle tip to the skin of the patient. After the wedge-like operating member 104 passes over a package 125 and clears the package 125, the top 121 of the package 125 springs upwardly due to the natural spring-effect of the plastic material from which it is made, to the condition shown by package 150 in FIG. 18.

As mentioned above, the rectangular members can be factory sealed in cellophane or other similar materials. To use same, the cellophane or other sealing materials need not be removed from the rectangular members before use. The rectangular members, with their cellophane or the like seal, can be inserted in the cassette 110 as shown in FIG. 12. When the operating member 104 passes over the rectangular member to force the needle 122 downwardly, the needle automatically punctures the cellophane plastic sealing material to apply the allergen on the tip thereof to the skin of the patient. This facilitates use and maintains sterility since the cellophane sealing material need not be removed prior to use of the apparatus.

A plurality of the units 100 can be arranged side-by-side, each unit 100 having its own operating member 104. Alternatively, the operating members 1-4 for each of the units 100 can be ganged together (as shown in FIG. 19) so that one movement by the operator will move all of the operating members 104 for each of the units 100.

Figure 10A:
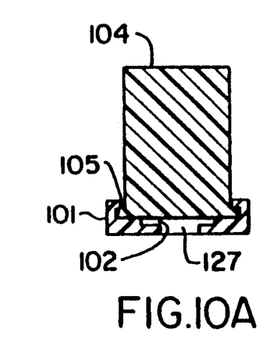
FIG. 10A is a sectional view taken along the line 10A—10A in FIG. 10.
Figure 19:
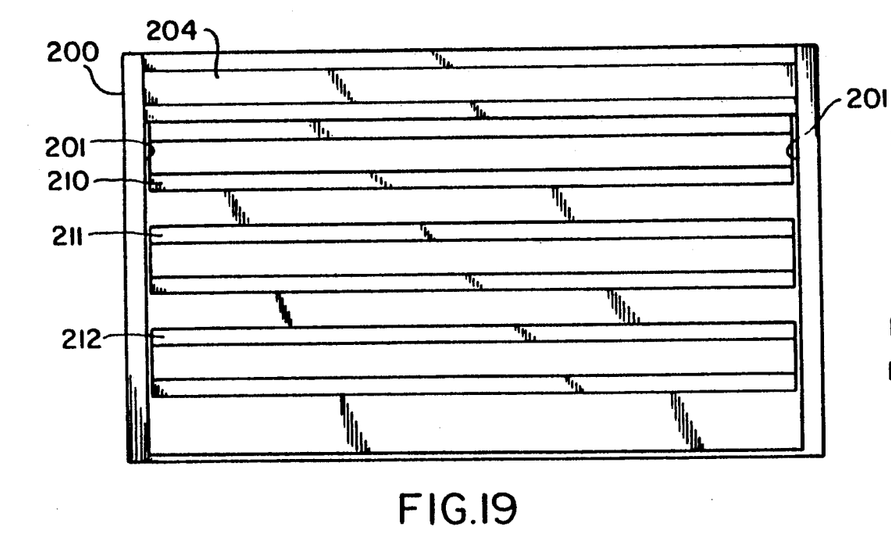
FIGS. 19 and 20 are top and side views, respectively, of a further modified embodiment of the invention.

As seen in FIG. 19, a embodiment having a plurality of cassettes uses a single widthwise movable operating member 204. The base unit 200 comprises a pair of elongated guide rails 201 within which side projections of operating member 204 are slidably received, in the same manner as shown in FIG. 10A. The operating member 204 has side projections 205 which fit within the guide grooves of the rails 201.

The base member 200 comprises a plurality of troughs 210-212 (in this embodiment three troughs) which are shaped similarly to the troughs in FIGS. 11 and 12. The cassettes which are insertable in the troughs 210-212 are different from the cassettes shown in FIGS. 11 and 12, and are shown in FIG. 22.

Figure 20:
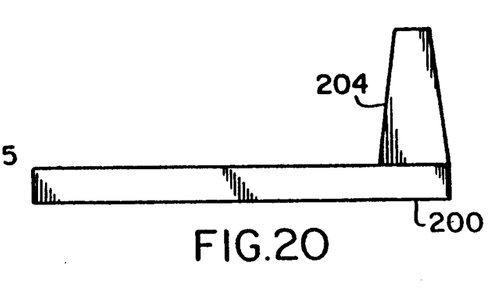
Figure 21:
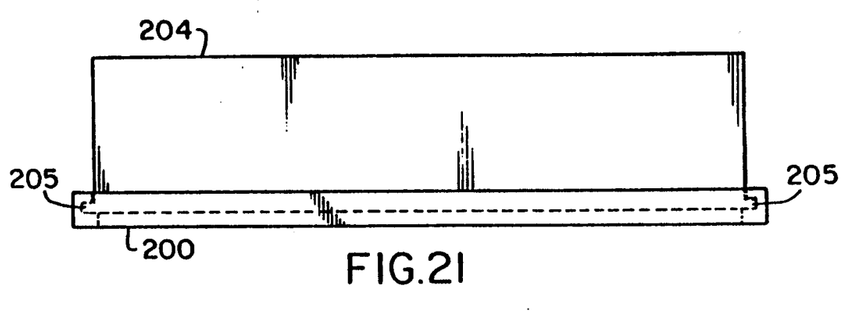
FIG. 21 is an end view of the operating member of the embodiment of FIGS. 19 and 20.

Referring to FIG. 22, a cassette for use with the embodiment of FIGS. 19-21 comprises an elongated base member 220 having a resiliently connected inclined top or cover member 221. The elongated top member 221 has a plurality of needles mounted thereon as shown in FIG. 22, the needles preferably having allergens placed on the needle tips or as shown in FIGS. 25-27 at the factory during manufacture. The cassette of FIG. 23 is also preferably factory sealed with a puncturable material. The cassette also has an elongated groove-like opening 222 through which the needles 223 pass when the top member is pressed downwardly in the direction of the arrow C in FIGS. 22 and 23. Preferably, a cassette has from 10-12 needles, each tipped with different allegerens, although any number is possible.

In use, the cassettes are placed within the troughs 210-212 of the base unit 200 of FIG. 19. Then, the operating member 202 is moved in the direction of the arrow D in FIG. 22 so as to press the cover or top members 221 downwardly in the direction of the arrow C in FIG. 23, thereby causing all of the needles 223 of a respective cassette to substantially simultaneously extend through the opening at the bottom of the cassette and pierce or prick the skin of the patient, thereby testing the patient with a plurality of different allergens (each on a respective needle) at substantially the same time. As the operating member 204 is moved further in the direction of the arrow D in FIG. 21, the next cassette placed in trough 211 is operated, thereby piercing the patient's skin with another plurality of needles. The operating member 204 is pushed further in the direction cf the arrow D to operate the cassette located in trough 212 in the same manner.

The embodiment of FIGS. 19-24 is advantageous in that a single factory-prepared sealed cassette contains a plurality of allergens on respective needles or as in FIGS. 25-27. This eliminates the necessity of the operator loading each cassette with respective allergen carrying member, as is required in the embodiment of FIGS. 9-14. However, the embodiment of FIGS. 9-14 is advantageous if the operator wishes to test the patient for only a few different allergens, or if it is desired to test the patient with specific allergens which are not included in the factory-prepared large cassette of FIGS. 23 and 24. Moreover, there may be cases where the large cassettes of FIGS. 23 and 24 contain allergens which are known to be harmful to a particular patient. In such a case, the embodiment of FIGS. 9-14 is desirable since the operator can load the apparatus with only those allergens for which it is specifically desired to test the patient. It should be clear that various modifications and alterations can be made to the embodiments of the invention discussed above. For example, the rectangular allergen packages 125 of FIGS. 15-17 could be used in the embodiment of the invention shown in FIGS. 1-4. In this case the height of the base number 30 can be reduced since the packages 125 are substantially smaller than the packages 40 of FIGS. 5 and 6. Moreover, the base 30 of FIGS. 1-4 can be modified to delete the walls 50,61 between the respective compartments, and one single elongated compartment could be provided. Such a single elongated compartment could receive a cassette such as shown in FIG. 23. The cover 31 of such a modified embodiment need not, in this case, be provided with the projections 36, since the cover could merely press down the upper member 221 of the cassette of FIG. 23 to cause the needles 223 to project from the bottom of the base 30 to prick or pierce the skin of the patient.

A modified allergen containing package according to the present invention is illustrated in FIGS. 25 and 26. As seen in FIG. 25, the package comprises a base member 160 having a quantity of an allergen substance 163 on the upper surface thereof. A top member 161 is hingedly or pivotally connected to the base member 160, in the same manner as in FIGS. 15-17. A needle 162 projects downwardly from top member 161. During operation, when the top member 161 is pressed downwardly, the needle 162 passes through the allergen material 163 and then punctures the lower surface 160 to then proceed to prick the skin of the patient. The needle 162 picks up sufficient allergen 163 for the allergy test. The central portion of base member 160 in the vicinity of the allergen 163 can be made of a weaker material which may be more easily puncturable by the needle 162.

FIG. 27 shows a modified embodiment having a pouch or cup-shaped member 173 for containing an allergen. In use, the needle 162 passes through the cup-shaped member 173 to contact the allergen contained therein, and continues to puncture the bottom of container 173 to then proceed to prick the skin of the patient and apply the allergen to the pricked skin. The cup-shaped member 173 is formed of an easily puncturable material so that the needle 172 can relatively easily pass therethrough.

The allergen containing package of FIGS. 5 and 6 can be similarly modified so that the allergen is contained at a lower surface portion thereof so that the needle contacts the allergen upon passing downwardly.

Also, the embodiments of FIGS. 25-27 are preferably sealed in a cellophane-like material for sterility.

Figure 24:
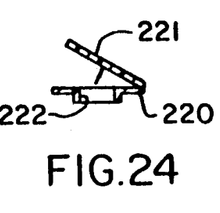
FIG. 24 is a sectional view of the cassette taken along line 24—24 in FIG. 23.

The embodiment of FIGS. 23 and 24 can be modified similarly to FIGS. 25-27, as should be apparent.

Figures 28, 32:
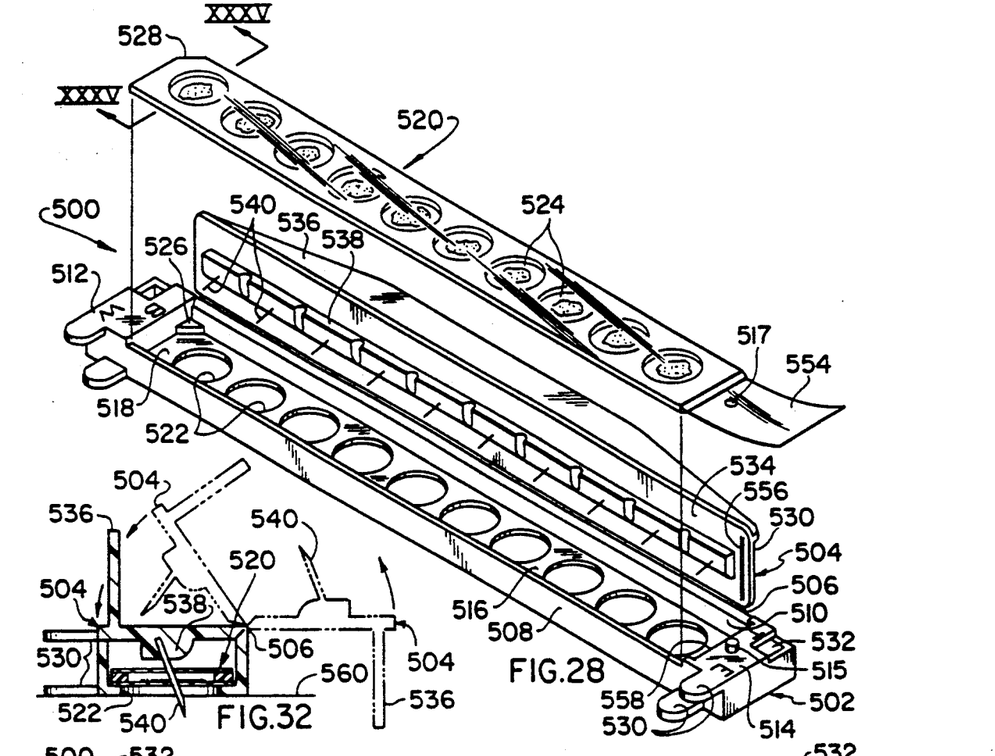
FIG. 28 shows an exploded isometric view of another embodiment of the present invention.
FIG. 32 is a sectional view of one unit, in sequence presentation, taken along line XXXII—XXXII in FIG. 29, and drawn to a larger scale.

FIG. 28 shows an allergen applicator device 500 which comprises a base member 502 and a cover member 504 pivotally connected to base member 502 by means of a living hinge 506. Base member 502 has a front wall 508, a rear wall 510, a left end member 512, and a right end member 514 which combine with bottom wall 516 to form a nest or compartment 518. Nest or compartment 518 is designed to receive an allergen strip 520 to be described in detail hereinafter with reference to FIGS. 33-35.

An array of circular openings 522 is formed in the bottom wall 516 so that the circular openings 522 are in registration with a similar array of positions 524 of allergen strip 520. As seen in FIG. 28, an orientation member 526 is affixed in the upper left corner of compartment 518 adjacent the plane of bottom wall 516. On allergin strip 520, the "upper left" corner is cut away at 528 in a shape similar to member 526. Orientation member 526 cooperates cutaway 528 to allow the user or manufacturer to mount the allergen strip 520 in the unit 500 with only one orientation.

Figure 29:
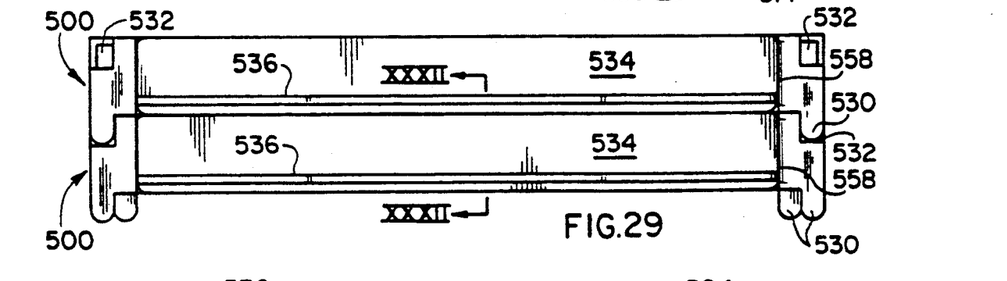
FIG. 29 shows a plan view of a double unit comprising two units of FIG. 28 coupled in tandem.
Figures 30, 31:
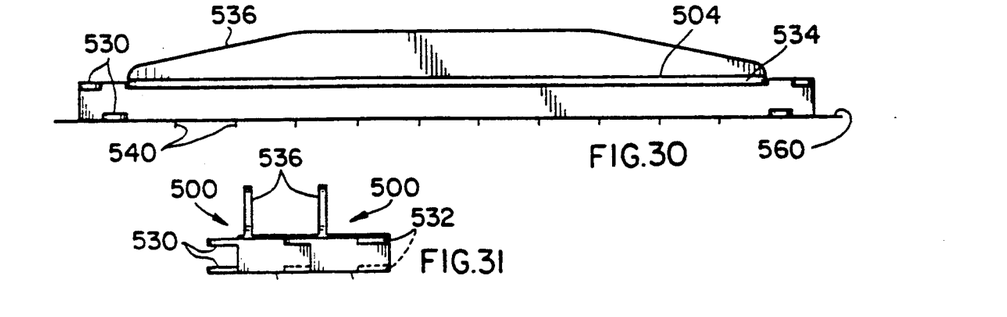
FIG. 30 is a front view of the embodiment of FIG. 29, shown in an operative position.
FIG. 31 is a right end elevation of FIG. 29.

End members 512 and 514 each has a pair of forward extending horizontal tabs 530 located to frictionally engage suitable cut-outs or receiving areas 532 on the rear portions of end members 512, 514 of an adjacent similarly oriented applicator unit 500, as shown in FIGS. 29 and 31. Tabs 530 and cut-outs 532 allow for tandem interlocking of two or more (only two are shown in FIGS. 29 and 31) applicators 500 to each other so that an orderly pattern of applicators allergens (to be explained later) may be rapidly and accurately applied to a test site on the patient. Other interconnection devices between units 500 can be provided in addition to or instead of tabs 530. Also, two or more units 500 could be fabricated as a single unit if desired.

Cover member 504 has, as its main part, a substantially planar member 534 on whose outboard side is a perpendicular, fin-like extension shaped to form a handle or operating member 536. On the inner side of member 534 is a shoulder-like projection 538 into which an array of pricking or piercing needle-like members 540 is embedded in respective registration with bottom wall openings 522.

FIG. 32 shows in 2-dot broken line a fully opened cover member 504 in the "as molded" profile position. A 3-dot broken line shows an intermediate position of cover member 504, and finally in solid line is shown the fully closed position of cover member 504 relative to base member 502 with pricking or piercing members 540 extending through respective openings 522 and extending out of the bottom 516 of base member 502 in a position to prick or scratch the skin of a patient to apply allergen thereto.

Figures 33, 34, 37, 38, 38A, 39, 42, 49:
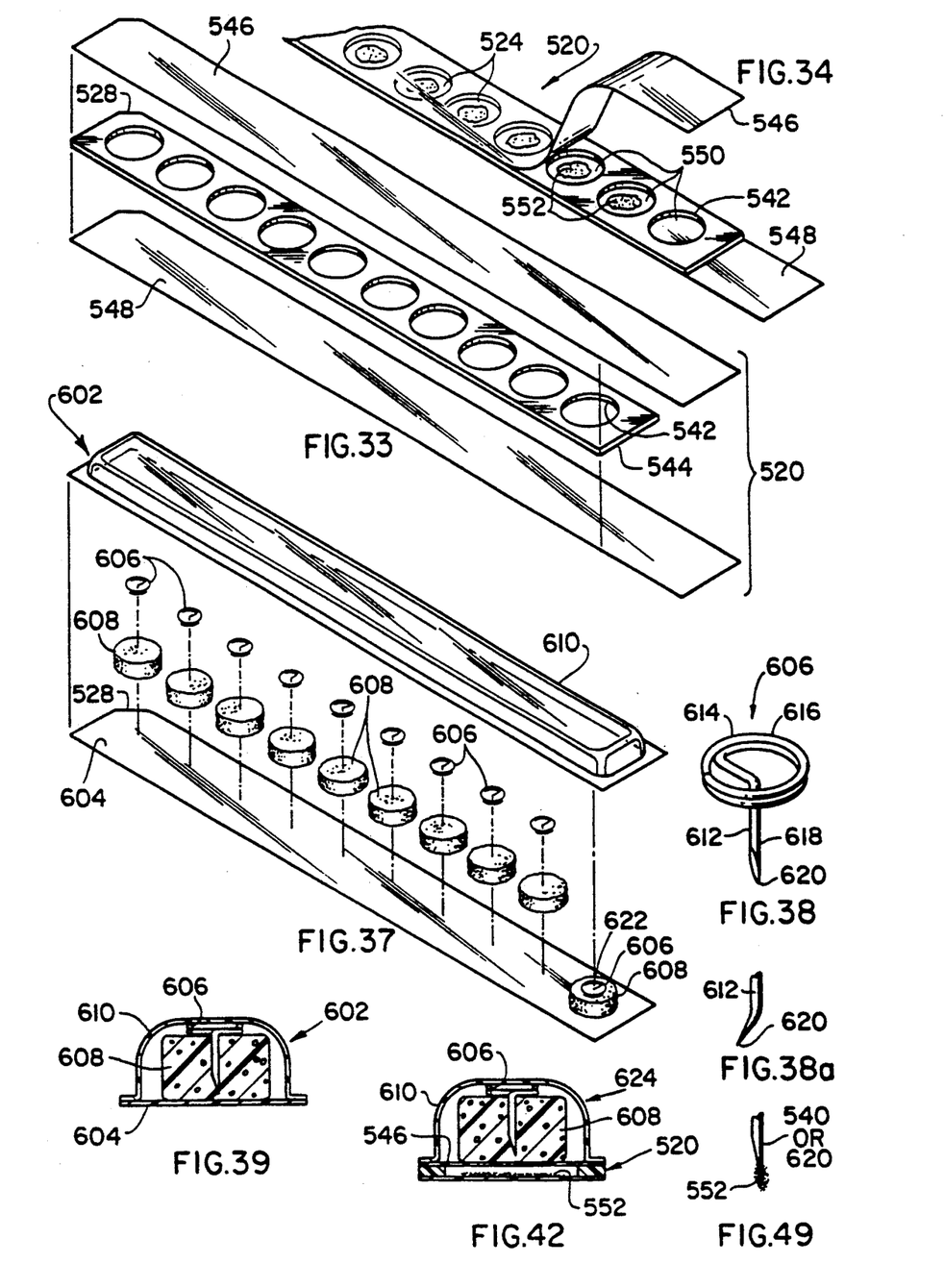
FIG. 33 is an exploded isometric view of an allergen strip used in the embodiment of FIG. 28-32 and another embodiment of the invention.
FIG. 34 is a view similar to FIG. 33 showing the allergen strip in an almost completely assembled state.
FIG. 37 is an exploded isometric view of a pricking or piercing element pack used in the embodiment of FIG. 36.
FIG. 38 is an enlarged perspective view of the individual pricking or piercing element used within the pack of FIG. 37.
FIG. 38a shows a modified pricking or piercing element.
FIG. 39 is a sectional view of the pricking or piercing element pack taken along line XXXIX—XXXIX in FIG. 36, and drawn to a larger scale.
FIG. 42 is a sectional view similar to FIG. 39 of a combination pricking or piercing element pack and allergen strip.
FIG. 49 illustrates a needle tip pre-coated with an allergen.
Figures 35, 36, 40, 41, 43, 44, 44A:
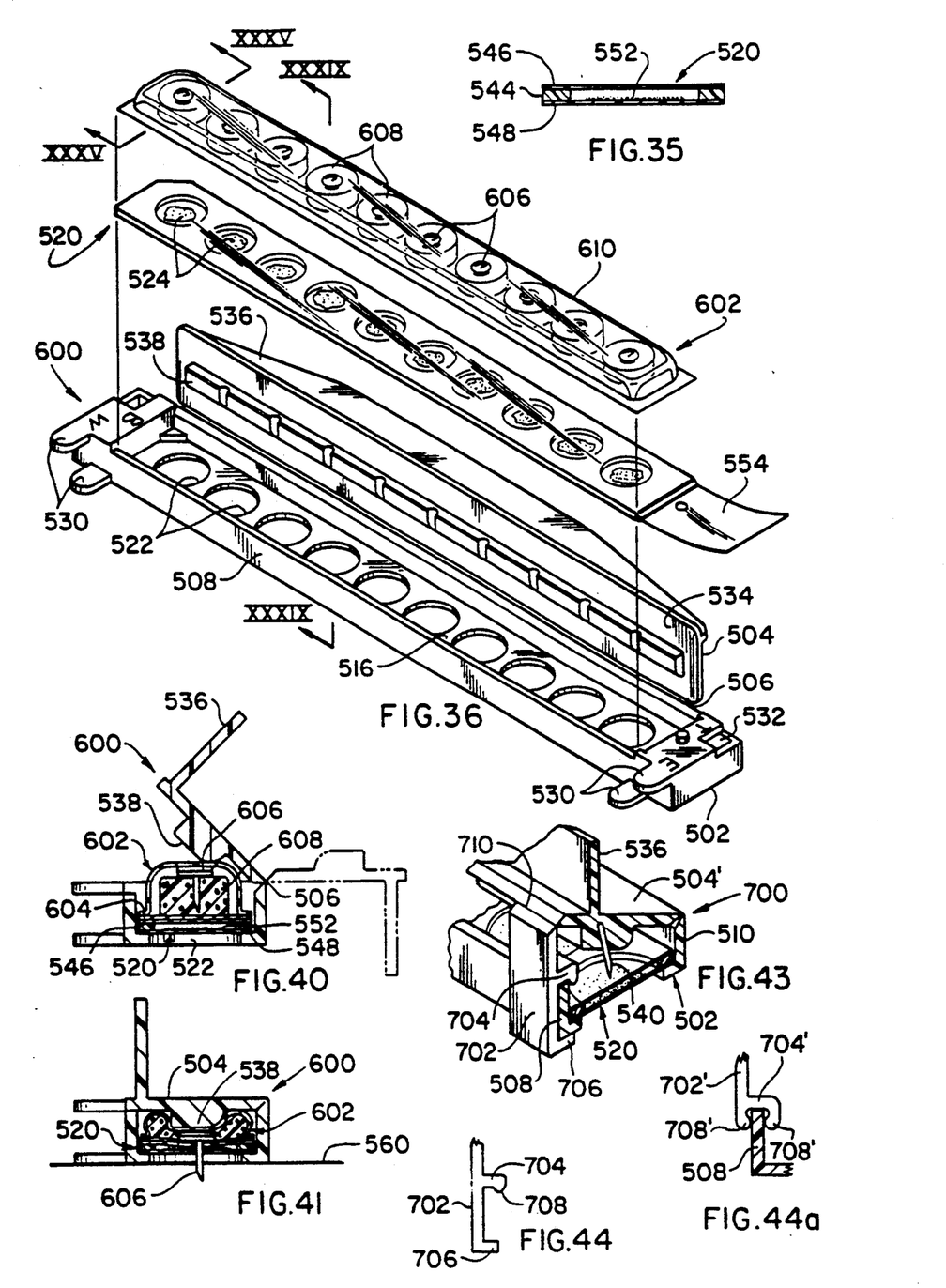
FIG. 35 is a sectional view of the allergen strip taken along line XXXV—XXXV in FIG. 28 and drawn to an enlarged scale.
FIG. 36 is an exploded isometric view of another embodiment of the present invention.
FIG. 40 is a sectional view, in sequence presentation, taken along line XXXIX—XXXIX in FIG. 36.
FIG. 41 is a sectional view similar to FIG. 40 showing components in final position.
FIG. 43 shows a modified embodiment with a mechanism for holding the cover of the device in a fixed position.
FIG. 44 illustrates an enlarged detail of the locking mechanism of FIG. 43.
FIG. 44a illustrates a modified locking mechanism of FIG. 43.

FIG. 33-35 show an allergen strip 520 in detail. Similar to the openings 522 in FIG. 28, an array of openings 542 is provided in elongated body member 544 of the allergen strip 520 so that when the allergen strip 520 is installed in the compartment 518 of base member 502, the openings 542 are in substantial registration with the openings 522. Elongated body member 544 is made of inert plastic and supports an upper 546 and a lower 548 thin transparent film. Thin films 546, 548 need not be transparent. When allergen strip 520 is assembled, lower film 548 is adhered to the lower face of member 544, thus forming shallow pockets 550 along member 544. According to prescription or to a pre-set format, a variety of allergens 552 is then applied individually to each of the pockets 550. The allergens may be in the form of a paint, gel, paste, slurry, or the like, and may be just a sample of the allergen diluent. When all pockets 550 have allergen applied to thereto, the upper film 546 is sealed to the upper face of member 544 which forms sealed positions 524 of pockets 550 with respective allergens 552 located and sealed therein.

In FIG. 33, on the right hand ends of films 546 and 548 there is formed an excess length of films 546,548. This is done intentionally to form a flexible ejection tab 554 (FIGS. 28 and 36) on the end of allergen strip 520. In connection with tab 554, note that the right inboard corner 556 of cover member 504 and the upper inboard corner 558 of end member 514 are rounded to accommodate tab 554 when cover member 504 is in the closed position. As seen in FIG. 28, a pin 515 may be provided on the upper surface of end member 514 which is to be inserted into a hole 517 on tab 554 to engage the tab 554 with the base member 502. This also serves as another orienting means.

In use, a selected allergen strip 520 is snugly fitted into compartment 518 either by the user or at the factory. If multiple application units 500 are to be used in tandem, they are also loaded with suitable allergen strips 520. Such multiple units 500 are then coupled together in specific order as shown in FIGS. 29 and 31. The loaded unit(s) 500 is located on the patient's skin and then handle 536 is used to bring cover(s) 504 to final position as shown in solid lines in FIG. 32 and as also shown in FIGS. 29, 30 and 31. In so doing, pricking or piercing members 540 are caused to pass through upper film 546, allergen 552, lower film 548 and to prick or scratch (or pierce, if desired) the patient's skin 560 (see FIG. 5). The pricking or piercing members 540 will carry a small amount (but sufficient for the purpose) of each allergen 552 to a registered position on or into the patient's skin 560 for possible reaction and observation at a later time.

The unit(s) 500 may be removed in their closed position (or in a slightly open position) and disposed of intact. However, if it is desired to re-use the unit(s) 500, after removal from the skin of the patient, the cover 504 is opened and used allergen strip 520 is removed from compartment 518 by grasping tab 554. Unit(s) 500 may then be thoroughly cleaned and sterilized before reloading with new allergen strips and reused.

FIG. 36 shows another embodiment of an allergen applicator 600, wherein allergen strip 520 is utilized exactly as previously described and applicator unit 600 is the same as applicator unit 500 except that pricking or piercing members 540 are deleted. All other details are the same as before in regard to the allergen strip 520 and applicator unit 500.

Figures 45, 46, 47, 48, 48A:
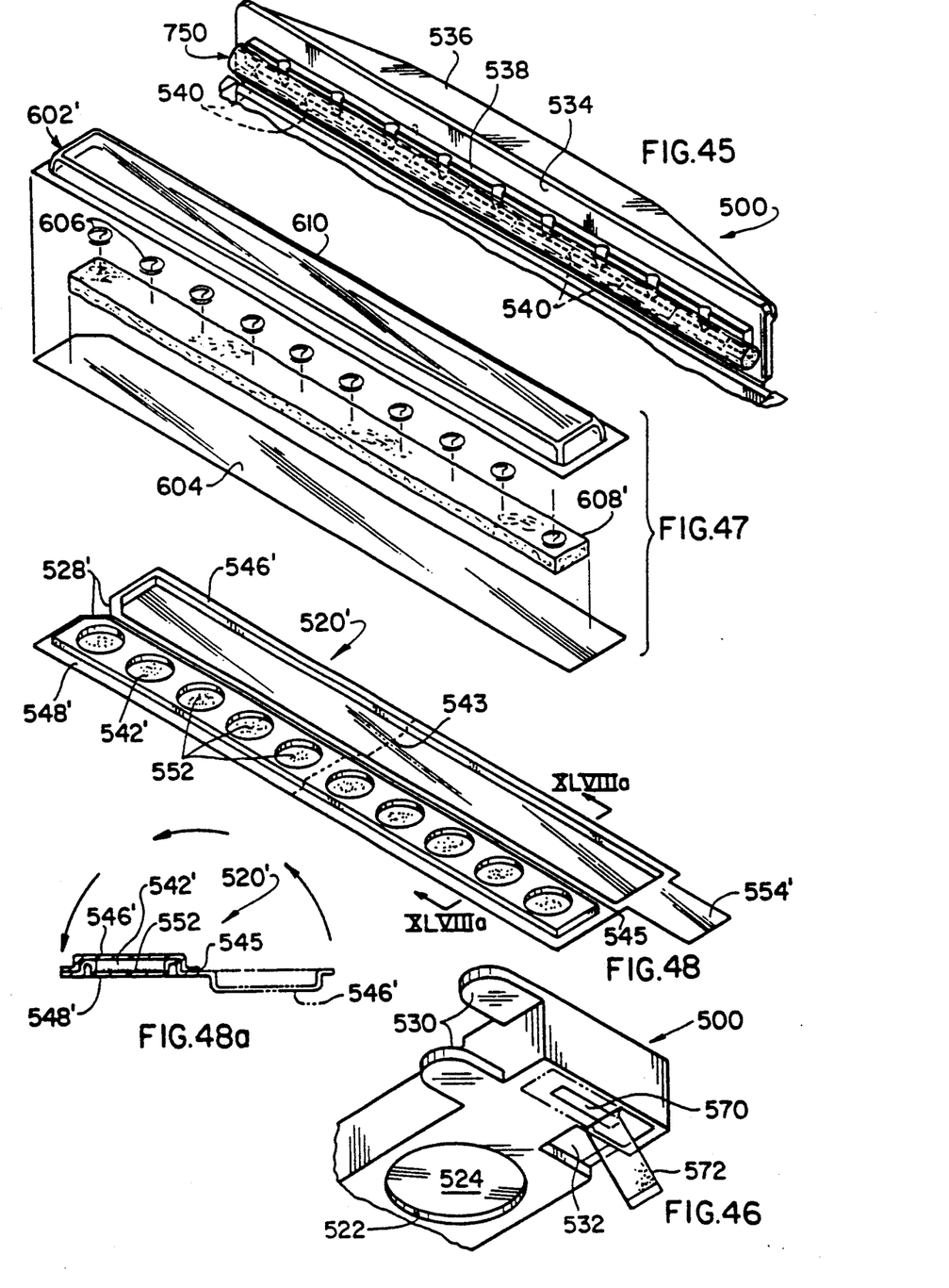
FIG. 45 illustrates a protective device for the pricking and piercing members.
FIG. 46 illustrates a skin marking arrangement.
FIG. 47 illustrates a pricking and piercing member package similar to that of FIG. 37, but of modified construction.
FIGS. 48 and 48a illustrates a modified allergen strip.

The pricking or piercing means in the embodiments of FIG. 36 is an elongated pricking or piercing element pack 602, somewhat like allergen strip 520. As best seen in FIG. 37, Pack 602 is comprised of lower sheet 604, an array of pricking or piercing elements 606, a like array of element supports 608 and a bubble pack closure member 610. Bottom sheet 604 can be of inert material as in the element supports 608. Supports 608 are discs of soft, yieldable foam plastic (or the like) but, as shown in FIG. 47, supports 608 could be replaced by one continuous generally rectangular foam (or the like) strip 608', if desired.

In FIG. 38 the pricking or piercing element 606 is detailed. Formed of stainless steel or other suitable wire 612 approximately two full turns 614 are shaped to effectively form a "flange" 616 which may be coaxial with leg 618. Leg 618 need not, however, be coaxial with flange 616. Pricking or piercing tip 620 can be formed by cutting leg 618 at a "flat" angle. The tip 620 can be bent as shown in FIG. 38a to provide more positive pricking of the patient's skin when the device is actuated.

As shown in the right hand position 622 of FIG. 37, pricking or piercing elements 606 are inserted into supports 608 which are placed on or secured to bottom sheet 604 in registration with compartment openings 522 and allergen strip positions 524. The bubble cover 610 is then sealed to sheet 604 maintaining pricking or piercing elements 606 in sterile condition. The upper left corner 528 of bottom sheet 604 and the like corner (hidden) of bubble cover 610 is cut away to cooperate with element 526 to serve as an orientation means as previously described. The cover 610 can be formed in one piece with bottom sheet 604 so as to be pivotally connected at one side, for example as shown by members 546' and 548' in FIGS. 48 and 48a.

FIG. 39 shows the relation between the components of the pricking or piercing element strip 602 of FIG. 37.

The use of applicator 600 is best shown in FIGS. 40 and 41. The allergen strip 520 is inserted into nest or compartment 518 of the applicator unit 600 of FIG. 36 followed by the insertion of pricking or piercing element pack 602. If multiple loaded applicators 600 are to be used in tandem, then they can be coupled in tandem fashion as explained hereinabove and located on the patient's skin 560.

Application of allergens takes place when the cover 504 is swung, via handle 536, about living hinge 506 and cover 504 reaches the closed position (see FIG. 41). In so doing, cover shoulder 538 is caused to bear down on and crush the upper portion 620 of pricking or piercing element pack 602 which drives elements 606 through bottom sheet 604, upper film 546, allergen 552, lower film 548 and into the patient's skin 560 by pricking the skin 560 with the pricking or piercing elements 606. As occurred with the applicator 500, a small amount (but sufficient for the purpose) of allergen 552 is carried on or into the patient's skin for possible reaction and later observation.

At this point, applicator units 600 can be removed from the patient, and either opened and emptied for reuse, or disposed of. It is pointed out that tab 554 now acquires the additional function of helping to remove pricking or piercing element pack 602 from nest or compartment 518 after use. Applicator units 600 can be sterilized and reloaded for reuse. As a further variation, a combined pricking or piercing element pack and allergen strip 624 is shown in sectional view FIG. 42. In this presentation, pricking or piercing element supports 608 are secured directly to upper film 546 of elongated allergen strip 520. Pricking or piercing elements 606 are positioned as shown and bubble cover 610 is also secured to upper film 546. The combined insert 624 minimizes handling, eases loading and reduces costs as bottom sheet 604 is no longer required.

In the interest of maintaining sterile conditions, all of the above components may be packaged (not shown) individually, in sets, or in bulk quantities as found to be most functional, and suitably sealed in easily openable packages as desired.

When using the embodiment of FIG. 28, it is desirable that a protective mechanism be provided to prevent the practitioner or the user from inadvertently piercing their skin with the pricking or piercing elements 540. Such inadvertent piercing or touching of the pricking elements 540 by the user or practitioner could create a danger to the user or practitioner and/or also could contaminate the pricking or piercing elements 540. This can be avoided by providing, as shown in FIG. 43, a locking member 702 having spaced apart projections 704, 706 thereon. The spaced apart projections 704, 706 are adapted to extend over the front side wall 508 of the unit 700, as schematically illustrated in FIG. 43 in the partially engaged state. FIG. 44 shows an enlarged side view of the locking member 702 showing a snap-type projecting engaging member 708 extending from projection 704 for snapping over the upper surface of front wall 508 of the unit 700. The locking member 702 is secured to the cover member 504 by means of a living hinge 710.

One or more locking members 702 may be provided along the length of cover member 504 to fixedly secure the cover member 504 in the position shown in FIG. 43. This prevents the user from inadvertently contacting the pricking or piercing members 540 in a positive manner. Alternately, the locking member 702 may be a single member extending along substantially the complete length of cover member 504. The projections 704, 706 can correspondingly extend along the complete length of the coextensive locking member 702, or may be provided at spaced apart locations along the length of such elongated locking member 702. In the embodiment of FIG. 43, the cover member 504' is wider than the cover member 504 of FIGS. 28 and 36. The reason for this is so that the locking member 702 can properly engage the front wall 508 of the unit 700 when the cover member is locked in a partially open state as shown in FIG. 43.

In use of the FIG. 43 embodiment, after the allergen strip 520 is installed in the unit 700, the cover 504' is partially closed and the locking member 702 is pivoted downwardly about living hinge 710 to engage the front wall 508 of the unit 700, as shown in FIG. 43. To use the device, the device 700 may be placed against the skin of the patient, with the locking member or members 702 in the position shown in FIG. 43, the locking member or members 702 is then pivoted clockwise about living hinge 710 to become disengaged from front wall 508 of unit 700, and then the unit is operated in the same manner as described with respect to the embodiments of FIGS., 28 and 36. When using the locking mechanism of FIG. 43, the units 700 cannot be conveniently coupled together in tandem in the same manner as shown in FIGS. 29 and 31. In this case, the units would be coupled in tandem in back-to-back relationship with rear side walls 510 of adjacent units being adjacent to each other, in substantially the same manner as shown in FIGS. 29 and 37.

Figures 50, 51, 52:
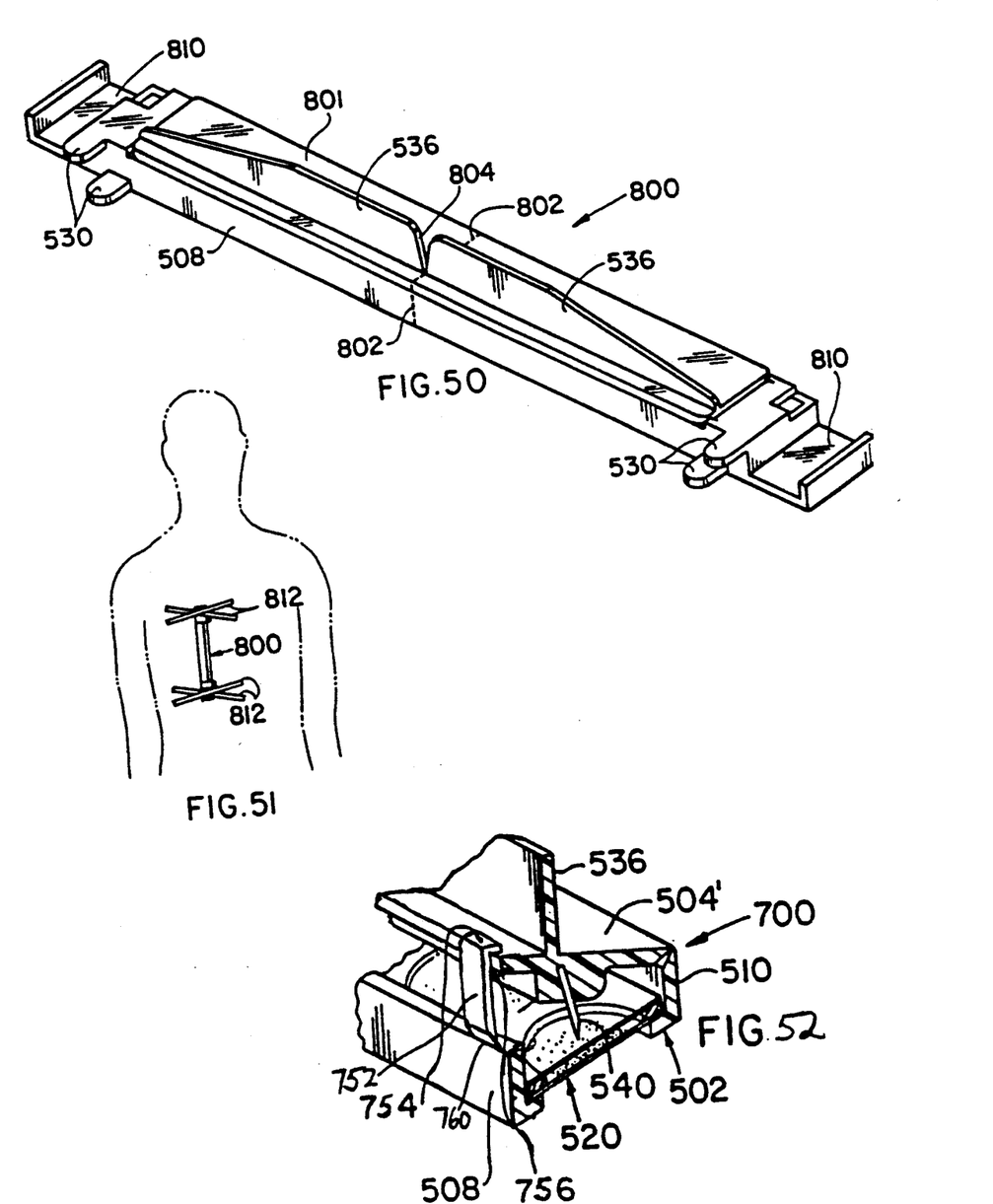
FIG. 50 illustrates an allergen application with means for securing same to the patient's body and with means for reducing the size thereof.
FIG. 51 shows the device of FIG. 50 mounted on a patient's body.
FIG. 52 shows another embodiment of a mechanism for holding the cover in a fixed position.

Other suitable locking arrangements for locking the cover 504, 504' of the units 500, 600, or 700 in a partially opened state may be provided, as desired. For example, as shown in FIG. 52, a locking member 752 similar to locking member 702 of FIG. 43 may be provided so that it extends from an upper edge portion of front wall 508 with a living hinge connection 760 therebetween so that it is pivotable to engage a free edge of cover member 504, 504' by means of spaced apart projections 754, 756 similar to projections 704, 706 shown in FIG. 43. Essentially, such a construction would operate in the opposite manner as shown in FIG. 43, but the devices could then be coupled in tandem as shown in FIGS. 29 and 31, since the locking member would not interfere with the adjacent andem unit.

According to another modification, the free end of locking member 702 can terminate substantially at the projection 704, as shown in FIG. 44a. In FIG. 44a, the locking member 702' has a first inwardly projecting projection 704'. Bumps or dimples 708' are provided at the bottom of locking member 702' for engagement with the upper end surface of front wall 508 of the unit 700, as shown in FIG. 44a.

Instead of the above-described locking members 702, 702', the piercing members 540 can be covered or protected by means of a foam (or equivalent) strip 750 as shown in FIG. 45. Still further a wedge (not shown) can be inserted between the cover and the body to keep the cover in fixed position. The wedge would be removed just prior to use, such a wedge can be made of hard plastic, soft plastic or foam, or other suitable material, and/or can be clipped or adhered in place so as to be easily removable by the user. Other protective mechanisms can be provided to prevent the practioner or the user from inadvertently contacting the pricking or piercing elements, 540 such as molded-in elements (preferably break-away) or other elements which can be connected to the basic structure.

In order to insure that the allergen applicator units 500, 600, 700 are oriented in the desired manner on the patient, so that the practitioner can ascertain the relative locations of the particular allergens being used, the units are preferably oriented always in the same way. As shown in FIG. 28, the right end of unit 500 has the symbol E (elbow) and T (top) thereon. The left end has the symbols W (wrist) and B (bottom) thereon. When used on the arm of the patient, the end of the device with the symbol E thereon is placed nearest the patient's elbow. When used on another body part, the symbol T represents "top". Thus, the practitioner can determine the relative orientation of the device on the patient.

In addition to the indicia E, T, or as an alternative thereto, as shown in FIG. 46, the undersurface of one end of the bottom surface of unit 500 (or of units 600, 700) may have a water soluble marking substance 570 (similar to a small stamp pad) thereon which is covered by a piece of peel-off tape 572. Just prior to use, the tape 572 is peeled off. When the device 500 is placed against the skin of the patient, the water soluble substance 570 marks (or stamps) the skin of the patient, thereby determining the relative orientation of the device on the patient.

Another method of orienting the device on the body of a patient is to provide the pricking or piercing members at one end thereof closer to one another. For example, the first two piercing or pricking members 540 at the right end of the device could be closer together than the others, thereby permitting the practitioner to visually determine the relative orientation by the condition of the patient's skin.

In FIGS. 48 and 48a an alternate embodiment of allergen strip 500 is shown as 520'. Strip 520' is vacuum formed in one piece (i"e. top member 546' is connected to bottom member 548' along fold line or hinge portion 545) of thin plastic. Wells 542' are formed in bottom member 548' similar to openings 542 of strip 520 for the application of allergen(s) 552 within. Top member 546' is made to nest neatly over bottom member 548' and is sealed thereon after folding about hinge line 545 to form a finished sealed strip. Appropriate cuts 528' allow for mating with the members 526 (FIG. 28) to provide for the orientation feature previously discussed. A breakaway perforation 543 is provided at midpoint and will be explained hereinafter in connection with FIG. 50. On the right hand end of top member 546' is an extension 554' which functions as did extension 554 in strip 520. The extension 554' could extend from bottom member 548', as should be apparent.

FIG. 49 shows the tip of pricking or piercing element 540 or similarly the tip 620 having an allergen 552 applied directly on the point portion. In this embodiment it becomes obvious that neither allergen strip 520 nor strip 520' would be required in the 500 and 600 applicator, since each pricking or piercing element in the unit 500 would have its associated allergen substance precoated thereon at, for example, the factory. Such units 500 would be sealed in a plastic or other bag-like covering to maintain sterility.

In FIG. 50 is shown an allergen applicator 800 with cover 801 shown closed. The interior of applicator 800 may incorporate any of the allergen delivery systems described heretofore with reference to FIGS. 28-49. Applicator 800 has some optional features which enhance functional aspects beyond the point explained so far. At midpoint is a breakaway perforation 802 to be used in conjunction with half of allergen strip 520' when limited tests are to be performed. Although not shown, a similar breakaway perforation could be applied to allergen strip 520, similarly as shown in FIG. 48. Perforation 543 on strip 520' is coincident with perforation 802 on applicator 800. A convenience notch 804 has been added to handle 546, to facilitate separation. If desired, the perforation 802 could be provided only on the cover 801 so that only half of the cover 801 could be actuated, to obtain the same result. The location of the perforations 802, 543 can be varied along the length of the device. Alternatively, the allergen strips described above can be arranged with fewer allergens contained therein to enable specific tests with only a few substances to be performed, as desired. In such case, the embodiment of FIG. 36 is more desirable since the number of needles can be the same as the number of allergens being used.

Occasionally the allergist is called upon to administer tests to a hyperactive child, a palsied elder, or other difficult to treat patient. In such a case there can be a "location" problem. It may be necessary to secure the applicator on location before the pricking or piercing action. TO this end, as shown in FIGS. 50 and 51, applicator 800 has stirrup-like extensions 810 on either end. These extensions 810 allow for the application of adhesive tape 812 (preferably of the low-tack type) to hold applicator 800 in place as shown in FIG. 51. In addition to tape 812, or as an alternative thereto, when the applicator 800 is to be used on a limb of the patient, VELCRO strips (not shown) or elastic bands (not shown) may be used in conjunction with extensions 810 to secure the applicator in place.

An important advantage of the present invention is that the pricking or piercing of the skin is always done to a given skin penetration depth. Another important advantage is that the skin penetrations always have a given fixed spacing therebetween which does not rely upon operator judgment. The skin penetrations are appropriately spaced to separate allergen reactions from each other without overlap. The penetration depth is a function of the distance the various needles project downwardly from the lower surface of the device when they are actuated- Also, the skin penetration depth is replicable in a very accurate manner, without requiring highly skilled operators since the penetration depth is not a function of the skill of the operator, but is a function of the length of the needles and the other dimensions of the apparatus. Thus, repeatable results are obtainable when using the system of the present invention, thereby providing a highly accurate allergy testing system.

The term "allergen" is used throughout this specification and claims to denote the substance applied to a patient. However, the invention is equally applicable to antigens in general or to any other substance desired to be applied to the skin of a patient, and the term "allergen" as used in the specification and claims denotes antigens as well as allergens as well as said any other substance.

Various additional modifications and alterations can be made within the scope of the appended claims.

I claim:

1. An allergy testing apparatus and an allergen source strip for use in said allergy testing apparatus, said allergy testing apparatus including means for removably receiving an allergen source testing strip, said allergen source testing strip comprising:
   a carrier member having a predetermined plurality of allergen sources thereon at spaced apart positions;
   means for sealingly enclosing said allergen sources in said carrier member; and
   orientation means cooperatively coupling with a corresponding orientation means in said allergy testing apparatus for permitting receiving of said allergen source testing strip in said allergy testing apparatus in only a single given orientation.

2. The combination of claim 1, further comprising pricking means sealingly enclosed in said carrier member.

3. The combination of claim 1, further comprising piercing means sealingly enclosed in said carrier member.

4. The combination of claim 1, wherein said orientation means comprises a cut-off portion of said carrier member.

5. The combination of claim 4, wherein said carrier member has a number of corner portions, and said cut-off portion comprises a cut-off corner portion of said carrier member.

6. The combination of claim 1, wherein said orientation means comprises a pin on one of said allergen source testing strip and said allergy testing apparatus; and
   a pin-receiving hole in the other of said allergen source testing strip and said allergy testing apparatus.

* * * * *